(12) United States Patent
Fuller

(10) Patent No.: US 6,908,195 B2
(45) Date of Patent: Jun. 21, 2005

(54) THERAPEUTIC EYE AND EYE LID COVER

(76) Inventor: John Robert Fuller, 45, Thorn Park, Mannamead, Plymouth, PL3 4TF (GB)

( * ) Notice: Subject to any disclaimer, the term of this patent is extended or adjusted under 35 U.S.C. 154(b) by 0 days.

(21) Appl. No.: 10/491,389

(22) PCT Filed: Jan. 24, 2003

(86) PCT No.: PCT/GB03/00274

§ 371 (c)(1),
(2), (4) Date: Mar. 31, 2004

(87) PCT Pub. No.: WO03/061535

PCT Pub. Date: Jul. 31, 2003

(65) Prior Publication Data

US 2004/0237969 A1 Dec. 2, 2004

(30) Foreign Application Priority Data

Jan. 24, 2002 (GB) .............................. 0201563

(51) Int. Cl.[7] .............................. G02C 1/00

(52) U.S. Cl. ....................... 351/158; 604/291
(58) Field of Search ................. 351/158, 41, 62; 604/289, 290, 291, 194, 195

(56) References Cited

U.S. PATENT DOCUMENTS 5,363,153 A * 11/1994 Bailiff .......................... 351/78
5,368,582 A * 11/1994 Bertera ........................ 604/295

* cited by examiner

Primary Examiner—Hung Xuan Dang
(74) Attorney, Agent, or Firm—Melvin I. Stoltz

(57) ABSTRACT

A therapeutic eye and eyelid cover provides heated saturated air to the covered tissue and a transparent front (18, 19) to enable clear vision during use. The cover includes heating means (17) and means (22) for saturating the air enclosed against the face with water vapor, preventing evaporation from the eye and eye lids and enhancing heat transfer to the covered tissue. The transparent front is constructed to prevent condensation and maintain clear vision at all times during use.

14 Claims, 3 Drawing Sheets

THERAPEUTIC EYE AND EYE LID COVER

FIELD OF THE INVENTION

This invention relates to a therapeutic eye and eyelid cover and, in particular, to a device for enhancing tear quality by manipulating the local ocular environment.

BACKGROUND TO THE INVENTION

A functional tear film is necessary for ocular health and vision. Tear quality, quantity, lid closure and blink are all important in maintaining a lubricated ocular surface. The ocular surface is a complex and dynamic environment, disturbance of which can be multi-factorial.

The tear film is formed of three layers. In contact with the corneal epithelium is the innermost mucin layer, one function of which is its action as a wetting agent. The middle layer is aqueous and is derived principally from the lacrimal glands. It constitutes the bulk of the tear film. The most superficial layer is oily and is derived from the meibomian glands in the eyelid. Meibomian gland drainage is a vital component to the healthy tear film. There are approximately forty of these small structures in each upper lid and thirty in each lower lid.

During the blinking process, probably at the point of lid closure, lipid is released from the meibomian glands onto the tear film layer. The principal function of this oily layer is to prevent tear evaporation. (See Reference 1). Additionally, it enhances tear stability, prevents tear spillover, sebum contamination and helps seal the lids at night. A smooth lipid layer also provides an ideal surface for refraction and the creation of a sharp retinal image. (See Reference 2).

Meibomian gland dysfunction [MGD] may occur spontaneously or be part of an oculocutaneous disorder such as blepharitis, atopic keratoconjunctivitis or generalized sebaceous gland dysfunction. MGD is a major cause of ocular surface abnormalities and ocular discomfort. (See Reference 3).

MGD and consequent oily tear film disturbance is a frequent clinical problem. One of the typical features of MGD is meibomian gland orifice obstruction. One manifestation of obstruction is capping of gland orifices where the surface of the orifice becomes covered with a layer which can be pierced with a needle and allowed to drain freely. (See Reference 4). It is possible that the surface of the capped gland is covered with an oxidized and saturated and therefore solid lipid covering. An adequate release of the oily tear film depends on the physical drainage of the oily layer. The melting point range of meibomian oil is reported as 19.5 to 32.9° C. (See Reference 5). Release of lipid is also related to the lipid constitution and the interplay of the musculature of the eye lids and meibomian orifices which, on lid closure, physically expel the lipid onto the tear film.

Animal studies have shown that experimental obstruction of these meibomian glands leads to ocular surface abnormalities found in keratoconjunctivitis sicca [dry eyes]. (See Reference 6). Studies in human volunteers have demonstrated an increase in the tear film lipid layer following a program of manual expression. (See Reference 7). Contact lens patients with MGD who undergo Meibomian therapy of lid scrubs and massage have been shown to have an objective increase in tear quality. (See Reference 8). Tear stability is increased following expression of the meibomian glands in healthy volunteers. (See Reference 9). Therefore an increased lipid thickness leads to improved tear quality and patient comfort. An important factor in the release of lipid is the ambient temperature level as, at higher temperatures, lipids are more liquid. Therefore, if the temperature of the lids can be increased and, if necessary, mechanical manipulation of this soft tissue induced, then the balance can be tipped from blockage to drainage.

Current advice to patients with obstructive MGD is to place hot flannels over the eyelids and massage the lids to increase the drainage. However patients find this is inconvenient and poor patient compliance is therefore an obstacle to effective therapy.

Patients with aqueous deficient dry eye often have associated lipid layer abnormalities and would benefit from an improvement in their tear lipid layer. Dry eye patients would also benefit from an environment that minimizes evaporative loss.

It is accordingly an object of the present invention to provide a therapeutic eye and eyelid cover that can be used to enhance tear quality.

It is a further object of the present invention to provide a therapeutic eye and eyelid cover that can be used to benefit patients having the above conditions.

SUMMARY OF THE INVENTION

According to the present invention there is provided a therapeutic eye and eyelid cover which can be fitted against the upper part of the face of the user so as to cover the eyes and eye lids and to retain a body of air in the space between the cover and the upper part of the face of the user, the cover including means for saturating or semi-saturating and heating said body of air and for preventing evaporation from, and enhancing heat transfer to, the covered tissue of the user while at the same time, providing a clear visual axis for the user.

The physical properties of the body of air contained in this space can then manipulated to produce a desired response. Those variables that can be specifically controlled include:
a) Temperature—in normal operation, the temperature will be raised by a prescribed amount or to a controlled level.
b) Humidity—for routine treatment, the humidity will be raised to saturate the air held by the device against the face.
c) Pressure—it is possible to rapidly modulate the air pressure inside the device.
d) Chemical composition—although the principal constituent of the body of air retained by the device against the user's face is saturated air, provision can be made for the addition of therapeutic agents, should they be required on their own or combined with the water provided for humidification either directly into the space between the face of the user and the device, or in an insert placed within the space or in the water in a reservoir placed within the space.

The cover, which acts in use as a treatment device, includes a transparent surface and means for ensuring that the transparent surface does not become obscured by the effects of condensation so as to maintain unobstructed vision.

Use of the device allows a prolonged and comfortable period of efficient heat transfer and, if required, massage to the eyelids and meibomian glands while, at the same time, preventing evaporation from the moist surfaces of the eyes.

The unique design of the cover allows comfortable use with the preservation of a clear visual axis even when the enclosed air is heated significantly above the surrounding environment and saturated with water. The design of the device is such as to prevent the "fogging" of the lenses that would normally occur in such circumstances by providing for one or more of the following:

1) Raising the temperature of the inner optical surface above the air/water vapor mixture contained within the device. This can be achieved by heating or providing heated fluid to the space between an inner and outer glazed element, by direct radiated or conducted heat from the frame or body of the device in which any transparent components are mounted, or direct electrical heating by the incorporation of conductive components or layer of the appropriate electrical characteristics within the body or on the surface of the transparent components. It is also possible to provide the necessary heating of the transparent surface by circulating a suitable heated fluid through galleries within the transparent component or by a combination of one or more of the above methods.

2) Mechanical wiping or movement of an arm or seal relative to the transparent surface while in contact with that components internal surface.

3) Provision of a coating that reduces heat transfer and/or breaks down surface tension so as to minimize the effect of any condensation.

4) A continuously wetted surface to the inside of the transparent component.

The use of a humid environment enables a much more efficient heat transfer to the skin of the eye lids than would be possible with a dry environment. This effect not only enhances the heat transfer by conventional convection, conduction and radiation, but also enables a thermal siphon to become established. In this process, the water, by evaporating from the heated surface of the device and condensing on the relatively cool eye lids, transfers latent heat. Any excess water that condenses can then return to the device for reuse. This method of heat transfer allows the transfer of a larger quantity of heat at lower temperatures and, most importantly, prevents evaporation from the eyes. Transferring the heat at lower temperatures is advantageous in reducing the radiant heat.

The ability to change the air pressure inside the device by pumping air into or out of the enclosed volume trapped against the face using a small diaphragm or similar pump, preferably mounted inside a power control unit, is designed to produce a massaging effect. It is possible to control both the quantity of air delivered to or removed from the enclosed space within the device and the speed with which this occurs. This change of air pressure inside the device causes the exposed soft tissue and face-sealing ring to be slightly sucked into or pushed out of the opening in the device. The rapid "pulsing" of the air pressure inside the device will effectively cause the soft tissue and face cover to vibrate, in contrast to a slower pressure change that will produce a softer massaging effect. Another alternative is to provide this pressure modulating function by changing the pressure within the seal that lies in contact with the face of the user. The inclusion of a control system allows for the use of the device without this pressure modulating function or, if required, on an intermittent basis.

The device may include a temperature monitoring and control system that allows the temperature to be measured and compared with a reference temperature. The electrical power that flows to the heating system in the device is then automatically adjusted by the electronic control system. The temperature control set point may be fixed or adjustable for different eye conditions or effects.

The device preferably uses electrical power supplied by rechargeable storage batteries contained in a portable power and control unit. The small size and modest weight of this unit make the entire device portable enabling the wearer to complete many everyday activities at his or her leisure.

The device may be constructed with refractive components within its structure or it may be fitted with a mechanism to allow for the attachment of lenses or spectacles to correct the refractive error of any individual user and allow clear vision. For example, to correct presbyopia, a simple reading addition of between one and three diopters of plus correction could be incorporated into the transparent windows so that near work can be undertaken whilst wearing the device. To correct ammetropia, spectacles could be worn over or clipped onto the device or bespoke lenses incorporated into the transparent windows.

The portable power and control unit preferably includes a small electrical plug into which a mains electrical charging and power supply can be plugged. This unit then allows the charging of the batteries, or the use of the device directly from the mains electrical supply without the use of a battery, if required.

In order that the device can be adequately cleaned and used in a hygienic way on more than one person, means are preferably provided for the removal of any internal wet or absorbent element. This, if necessary, can then be replaced with a fresh component. The materials of construction of the head-mounted portion of the device are preferably such as to allow for exposure thereof to elevated temperatures inside an autoclave for the purposes of sterilization.

The device is preferably constructed in such a way as, or fitted with adjustment means, to enable it to be fitted comfortably to any normal adult head.

Further categories of patients that may benefit from use of the device are detailed below:

1. Meibomian gland blockage is more common in colder areas and is a frequent occurrence even in those individuals with subclinical MGD. Symptoms of ocular discomfort are common in older patients and one reason for this is related to poor tear quality. Use of the device will improve tear quality in these patients.

2. During ocular surgery, a significant problem is contamination by meibomian gland secretions, and debris from the eyelashes and eyelid margin. If, before ocular surgery, the drainage of the meibomian glands can be increased, improving the health of the eye and eye lids, ocular contamination and its risks of infection and inflammation can be reduced.

3. Blepharitis is a very common clinical problem. One important component of treatment is lid toilet to remove crusts, and bacteria and their antigenic load. This lid toilet will be facilitated by prior use of the device.

4. Contact lens intolerance may be reduced by the use of this device.

5. Patients with tear dysfunction secondary to mucin or aqueous deficiency may have their tear lipid layer morphology improved and tear quality and therefore ocular comfort can be enhanced.

DESCRIPTION OF THE PREFERRED EMBODIMENTS

Figure 1:
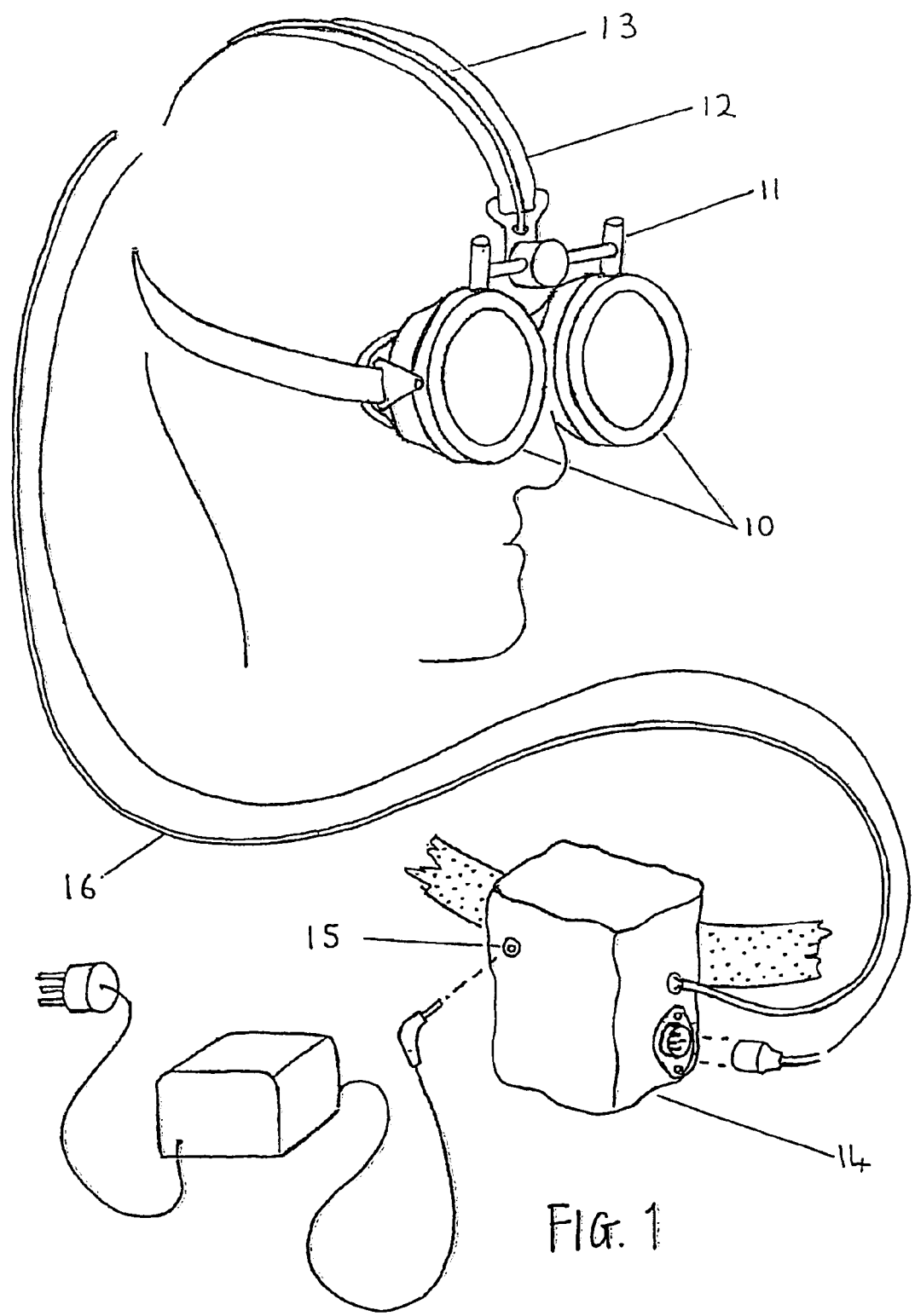
FIG. 1 shows the principal components of a pair of therapeutic goggles in accordance with the present invention, in which the temperature, humidity and air pressure can all be manipulated.
Figure 2:
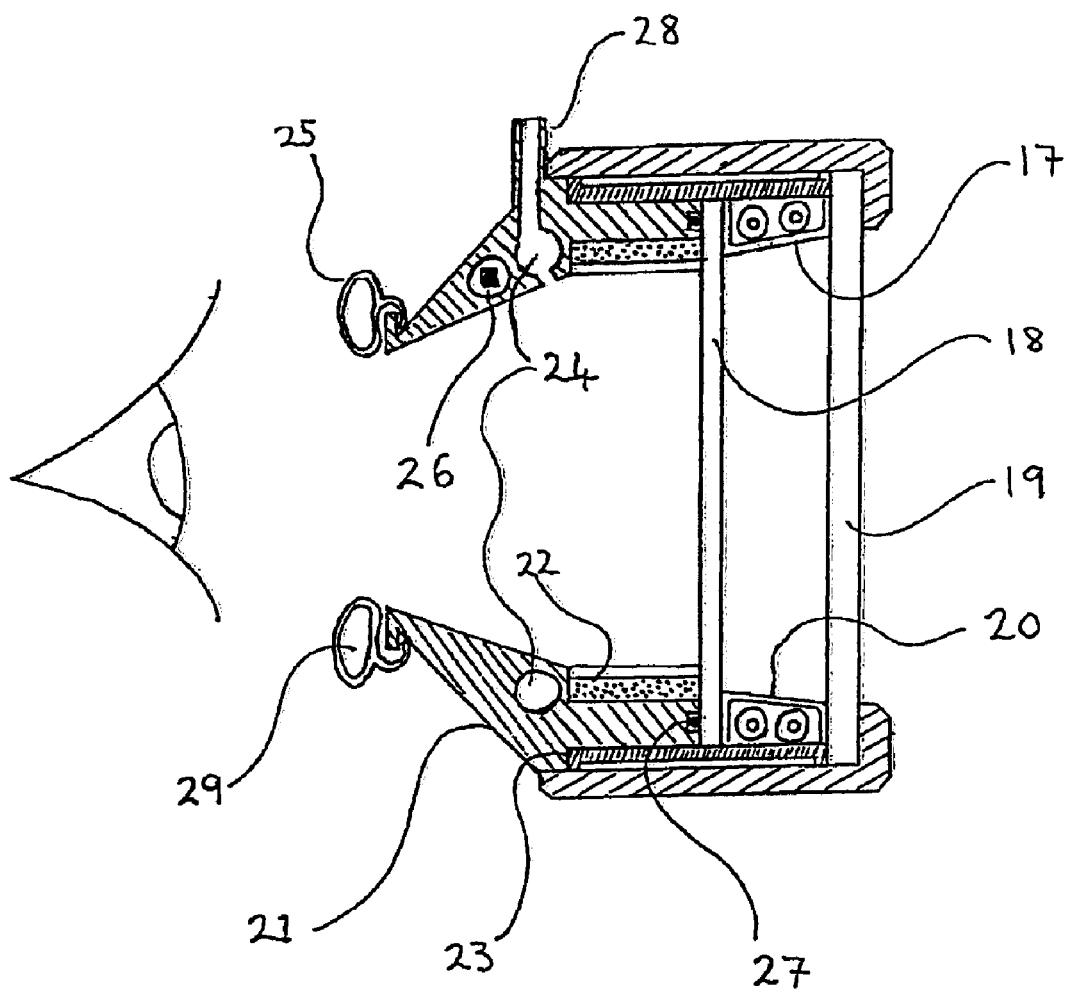
FIG. 2 is a sectional view through one ocular unit of the pair of goggles of FIG. 1.

The device shown in FIGS. 1 and 2 of the drawings comprises a pair of goggles including two ocular units 10 and an adjustable frame 11 that allows both the distance between the ocular units 10 and the angle at which they sit on the face to be adjusted. The goggles are secured to the head using an adjustable elastic strap 12. The central part of the strap 12 passes over the user's head and has a power and control cable 13 attached to it. The cable 13 plugs into a power and control unit 14 that either sits on a table or (as shown) is attached to a belt around the user's waist. This power control unit 14 contains a rechargeable battery, an on/off switch and temperature adjustment controls. The temperature and other performance data are displayed on a small liquid crystal display (not shown) on the housing of the power control unit 14. A socket 15 is provided for a battery charger to be plugged into the power control unit 14. A small variable speed and variable stroke diaphragm pump (not shown) in the power control unit 14 is connected to the goggles by a small diameter flexible hose 16.

Each ocular unit 10 includes two lenses 18 and 19 and a heating effect is provided by an electrical heating element 17 (FIG. 2), which is located in a space between the two lenses 18 and 19 of each ocular unit 10. This heats the air in this space, thereby warming the inner lens 18. The heating element 17 has a cover 20 having a matt black coating and providing some radiant heat to warm the central area of the inner lens 18. These two effects combine to ensure that the temperature of the inner lens 18 stays above the saturated air temperature inside the goggles' eye space. This prevents condensation and maintains a clear visual axis.

The inner lens 18 of each ocular unit 10 is mounted on a main body 21 and this is surrounded by an aluminum thermal backing ring 23 that extends up to the outer lens 19. A water reservoir 22 is contained within the main body 21 and is positioned adjacent the inner side of the inner lens 18. The reservoir 22 is filled with an absorbent medium.

The arrangement is such that, as the goggles warm up on starting, the plastic of the main body 21, which has a much higher coefficient of thermal expansion, expands and tightens up on the aluminum thermal backing ring 23, thereby providing enhanced heat transfer through to the main body 21 and the water reservoir 22. The backing ring 23 is of high thermal conductivity and carries much of the heat from the heating element 17 away into the body of the goggles and the water reservoir 22. The main body 21 of the goggles is of comparatively low heat capacity and hence allows the goggles to warm up quickly. Once the temperature of the main body 21 exceeds the surface temperature of the eye and the surrounding tissue, it is the tissue that tends to condense much of the vapor and hence absorbs the latent heat that it contains.

Any excess liquid that might condense on the tissue surrounding the eye or the body of the goggles will tend to drain back to the absorbent-medium-filled reservoir 22 where it is available for reuse.

To prevent excess radiant heat affecting the eye and the surrounding tissue, the heating element 17 is behind the inner lens 18 and is shielded by the main body 21 and the water reservoir 22 of the goggles, thereby preventing a direct line of sight with the eye.

The inner lens 18 is prevented from becoming too hot by being in contact with the water in the water reservoir 22.

Variation in the pressure, or "pulsing" of the pressure, in the ocular space, i.e. the space between the inner lens 18 of each ocular unit 10 and the associated eye and surrounding tissue, can be achieved by supplying or removing air from the ocular space through a circular manifold 24 and its associated hose connection 28.

There is a cavity within the main body 21 of each ocular unit 10 and this contains a microprocessor 26, which transmits data corresponding to the temperature at this location. The data from both ocular units 10 is used to control the electrical supply and hence the quantity of heat generated by the heating element 17. In this way, the temperature of the ocular environment is controlled.

There is a rubber sealing ring 27 located between the inner lens 18 of each ocular unit 10 and the associated main body 21, and the sealing ring 27 allows for any differential expansion of the main body 21 and the inner lens 18 while maintaining a watertight seal. A rubber ring 25 is fitted over the inner portion of the main body 21 of each ocular unit 10, and the cushion effect afforded by the rubber rings 25 allows the goggles to sit comfortably on the face.

As an alternative to providing the pressure modulating function via the manifold 24 and its associated hose connection, this function can be achieved by changing the pressure in the space 29 within each of the sealing rings 25 that lie in contact with the face of the user.

The medium-filled water reservoir 22 can be removable for cleaning purposes and the entire goggles (excluding the control/power unit and the electrical supply/charger unit) can be placed in a heated environment at up to 120° C. to ensure microbial cleanliness.

The reservoir 22 can serve as a means for adding therapeutic agents to the ocular space as a liquid instead of or combined with the water used to increase the humidity. The therapeutic agent may alternatively be a solid incorporated into a replaceable component within the device or as a vapor supplied to the device.

The principal material of construction is a lightweight engineering plastics material ensuring that the weight of the goggles is modest enhancing the comfort of the user.

The goggles can include refractive components within the structure of the cover or may be fitted with a mechanism (such as slots, clips or the like) to allow for the attachment of optical lenses or spectacles to correct the refractive error of any individual user and allow clear vision.

Figure 3:
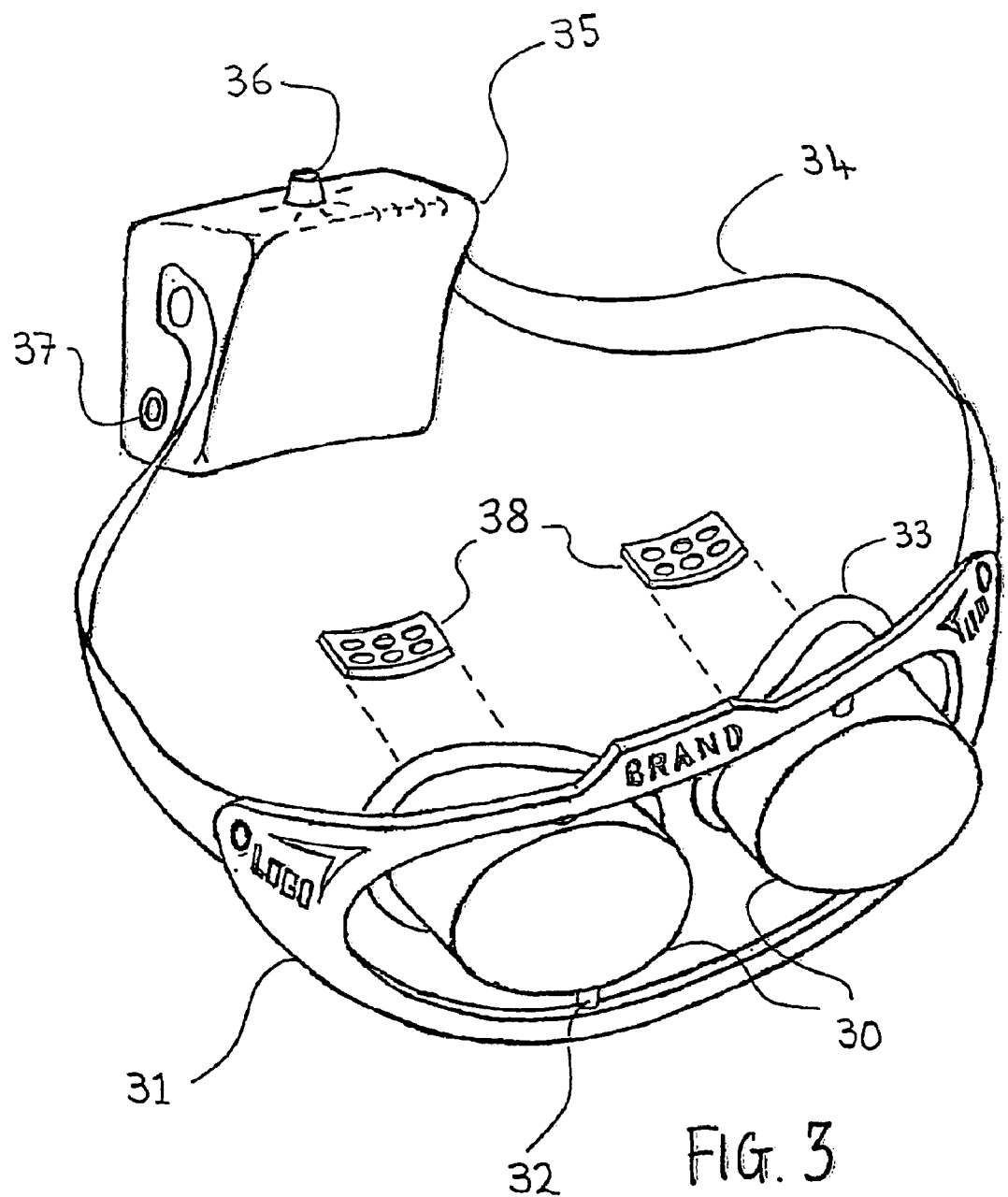
FIG. 3 shows a pair of goggles in accordance with the present invention designed to provide a warm saturated air environment for the eyes and to maintain clear vision with or without precise control of that environment.

The embodiment shown in FIG. 3 includes left and right hand ocular units 30 that fit comfortably on the face of the user and are held vertically in a support frame 31 by pins 32. A good seal is obtained around each of the eye cavities of the user by the use of soft rubber seals 33 and by the action of an elasticized strap 34 that pulls the goggles against the face of the user. The strap 34 also supports a battery and control unit 35 that sits at the back of the head of the user. The unit 35 contains rechargeable batteries and there is a knob 36 on the top of the unit 35 that can be rotated to operate an on-off switch and to control the level of power supplied from the unit 35 to the two ocular units 30. The batteries within the unit 35 can be recharged using a standard battery charger (not shown) connected to a socket 37. For clarity, the leads connecting the power unit 35 to the two ocular units 30 have not been shown in FIG. 3.

Each of the ocular units 30 of the embodiment of FIG. 3 includes a mounting for a removable insert 38 and each insert 38 contains the required quantity of water and/or the required therapeutic agent for each use of the goggles. The inserts 38 fit snugly in their mountings, which may be in the form of rebates inside the body of the goggles. Once in position, the inserts 38 are heated by an electrical heating element (not shown) contained within the main body 30. The electrical heating elements are arranged to raise the temperature of the inner lens of each ocular unit slightly more quickly and to a slightly higher level than the removable inserts in a manner corresponding to that described above with reference to the embodiment shown in FIGS. 1 and 2, to produce the "clear view steam room effect", and the desired response. The inserts 38 can be designed so that they can be removed and discarded after each use of the device.

The embodiment shown in FIG. 3 will be cheaper and easier to use at home while giving many of the medical benefits of the fully controlled glasses above. The absence of the pressure control option and the consequent reduction in power consumption give a further option of locating the battery control unit in the way illustrated.

Each of the embodiments shown in the drawings seals against the face of the user so as to trap a volume of air in each of the spaces between the face of the user and the lens systems. The air in each space is heated and humidified whilst, at the same time, the user is allowed to see clearly through each of the lens systems. If, of course, the device is in the form of a face mask as opposed to a pair of goggles, there will be just one space between the face of the user and the mask.

It is envisaged that the device of the present invention will be used intermittently. For example, it may be used two or three times a day for say five to ten minutes by some users, but more frequently and/or for longer periods by other users, depending on their individual requirements.

References:
1. Rolando M, Refojo M F, Kenyon K R. Tear water evaporation and eye surface diseases. Ophthalmologica 1985;190:147–9.
2. Dursun D Monroy D Knighton R et al. The effects of experimental tear film removal on corneal surface regularity and barrier function. Ophthalmology 2000;107:1754–60.
3. Shimazaki J, Sakata M, Tsubato K. Ocular surface changes and discomfort in patients with Meibomian gland dysfunction. Arch Ophthalmol 1995;113:1266–70.
4. Keith C G. Seborrhoeic blepharo-kerato-conjunctivitis. Trans Ophthalmol Soc UK 1967;87:85–103.
5. Tiffany J M, Dart J K G. Normal and abnormal functions of meibomian gland secretions. Roy Soc Med Int Cong Symp Ser 1981;40:1061–4.
6. Gilbard P G, Rossi S R, Heyda K G. Tear film and ocular surface changes after closure of the Meibomian gland orifices in the rabbit. Ophthalmology 1989;96: 1180–6.
7. Korb D R, Greiner J V. Increase in tear film lipid layer thickness following treatment of meibomian gland dysfunction. 1994 Lacrimal gland, tear film and dry eye syndromes Eds D A Sullivan, Plenum Press, New York.
8. Paugh J R, Knapp L L, Martinson J R, Milton M H. Meibomian Therapy in Problematic Contact Lens Wear, Optometry and Vision Science 1990;67:803–6.
9. Craig J P, Blades K, Patel S. Tear lipid layer structure and stability following expression of the meibomian glands. Ophthal. Physiol. Opt. 1995;15:5691–574.

What is claimed is:

1. A therapeutic eye and eyelid cover which can be fitted against the upper part of the face of the user so as to cover the eyes and eye lids to retain a body of air in the space between the cover and the upper part of the face of the user, the cover including means for saturating or semi-saturating and heating said body of air and for preventing evaporation from, and enhancing heat transfer to, the covered tissue of the user while, at the same time, providing a clear visual axis for the user.

2. A cover as claimed in claim 1, which includes at least one lens and means for preventing condensation on the internal transparent optical surface of said at least one lens.

3. A cover as claimed in claim 1, which includes means for heating the air held against the face by the cover.

4. A cover as claimed in claim 3, which includes two spaced lenses and in which the heating means is located between the two lenses.

5. A cover as claimed in claim 1, which includes means for increasing the humidity of the air held against the face by the cover.

6. A cover as claimed in claim 1, which include means for changing the pressure of the air over the covered tissue.

7. A cover as claimed in claim 1, which includes means for changing the pressure within a seal that, in use, contacts the face of the user.

8. A cover as claimed in claim 1, that includes a replaceable component designed for providing moisture and/or at least one therapeutic agent.

9. A cover as claimed in claim 1, which includes means for adding a therapeutic agent to said body of air.

10. A cover as claimed in claim 1, that has a portable power and control source either incorporated in the cover or as a separate transportable unit.

11. A cover as claimed in claim 1, which includes refractive components within the structure of the cover or is fitted with a mechanism to allow for the attachment of optical lenses or spectacles to correct the refractive error of any individual user and allow clear vision.

12. A cover as claimed in claim 1, having an electric mains supply unit to enable the device to be recharged at any time, or used directly from the mains electrical supply.

13. A cover as claimed in claim 1, which includes means to allow for the removal and replacement of any wet liquid retaining components.

14. A cover as claimed in claim 1, which includes a means of adjustment or is so designed to fit any normal size adult face with comfort.

* * * * *